US008438904B2

(12) United States Patent
Dimmler et al.

(10) Patent No.: US 8,438,904 B2
(45) Date of Patent: *May 14, 2013

(54) METHOD AND APPARATUS FOR VAPOR SIGNATURE WITH HEAT DIFFERENTIAL

(75) Inventors: Klaus Dimmler, Colorado Springs, CO (US); Thomas Moss, III, Colorado Springs, CO (US)

(73) Assignee: Sensorbit Systems, Inc., Austin, TX (US)

( * ) Notice: Subject to any disclaimer, the term of this patent is extended or adjusted under 35 U.S.C. 154(b) by 416 days.

This patent is subject to a terminal disclaimer.

(21) Appl. No.: 12/815,488

(22) Filed: Jun. 15, 2010

(65) Prior Publication Data

US 2011/0265554 A1 Nov. 3, 2011

Related U.S. Application Data

(60) Provisional application No. 61/330,414, filed on May 3, 2010, provisional application No. 61/330,415, filed on May 3, 2010, provisional application No. 61/330,416, filed on May 3, 2010.

(51) Int. Cl.
*G01N 7/00* (2006.01)

(52) U.S. Cl.
USPC ....... 73/31.05; 73/23.34; 73/31.01; 73/31.03; 73/31.06

(58) Field of Classification Search ........... 73/23.3, 73/23.34, 31.01–31.03, 31.05, 31.06
See application file for complete search history.

(56) References Cited

U.S. PATENT DOCUMENTS

| | | | |
|---|---|---|---|
| 3,815,405 A | 6/1974 | Dravnieks | |
| 6,006,583 A | 12/1999 | Hayashi | |
| 6,358,743 B1* | 3/2002 | Fox | 436/8 |
| 6,484,559 B2* | 11/2002 | Dodabalapur et al. | 73/23.34 |
| 6,575,013 B2* | 6/2003 | Bao et al. | 73/23.34 |
| 6,661,299 B2* | 12/2003 | Dodabalapur et al. | 331/57 |
| 6,834,530 B2* | 12/2004 | Kita et al. | 73/23.34 |
| 6,940,133 B1* | 9/2005 | Hopper et al. | 257/379 |
| 7,397,072 B2* | 7/2008 | Dodabalapur et al. | 257/226 |
| 2002/0116983 A1 | 8/2002 | Bao et al. | |
| 2010/0167959 A1* | 7/2010 | Johnson et al. | 506/39 |
| 2010/0323258 A1* | 12/2010 | Blackburn et al. | 429/428 |

OTHER PUBLICATIONS

Funtane et al., Nanocrystalline ZnO based MEMS Gas Sensors with CMOS ASIC for Mining Applications—International Journal on Smart Sensing and Intelligent Systems, vol. 1, No. 2, Jun. 2008.*

* cited by examiner

*Primary Examiner* — Hezron E Williams
*Assistant Examiner* — Hoang Nguyen
(74) *Attorney, Agent, or Firm* — Gordon Kessler

(57) ABSTRACT

An apparatus for sensing analyte is provided. The apparatus may include a plurality of sensor array columns, each sensor array column including a plurality of sensors, each sensor being adapted for sensing one or more parameters in reaction to the presence of one or more analytes and output a current therefrom in accordance with level of the sensed parameter, a heating element for selectively heating one or more of the sensor array columns, a Voltage Controlled Oscillator (VCO) array including a plurality of VCOs, each VCO adapted to receive an output current from one of the plurality of sensors from each of the plurality of sensor arrays and for and generating an output oscillation frequency in accordance with the level of the received output current, and a counter array including a plurality of counters, each counter adapted to receive an output from a corresponding VCO and count a number of oscillations over a predetermined time.

5 Claims, 7 Drawing Sheets

METHOD AND APPARATUS FOR VAPOR SIGNATURE WITH HEAT DIFFERENTIAL

CROSS REFERENCE TO RELATED APPLICATIONS

This application claims the benefit of U.S. Provisional Patent Application Ser. No. 61/330,414, filed May 3, 2010 to Dimmler et al. and titled METHOD AND APPARATUS FOR SENSING GASSES; U.S. Provisional Patent Application Ser. No. 61/330,415, filed May 3, 2010 to Dimmler et al. and titled METHOD FOR SENSING GASSES; and U.S. Patent Application Ser. No. 61/330,416, filed May 3, 2010 to Dimmler et al. and titled METHOD AND APPARATUS FOR SENSING GASSES, the entire contents of these three provisional patent applications being incorporated herein.

FIELD OF THE INVENTION

The present invention relates generally to the sensing of gasses, and in particular to the sensing of one or more gasses utilizing one or more hybrid composite silicon/organic field effect devices.

BACKGROUND OF THE INVENTION

There are a wide variety of sensor technologies available. While many of these technologies may be used to sense one or more gasses, each comes with one or more drawbacks or tradeoffs as compared with the present invention, most are not suitable for wide-spread portable applications for a variety of reasons. Many sensors are physically too large for portability. Others consume too much power to be reasonably operated by a battery. Others operate at very high temperatures making them difficult to use in portable applications. Still others are too expensive for wide-spread use, and many require training to use properly. A survey of existing mainstream sensor technology is outlined below.

Chromatography

A chromatograph is an apparatus that separates a complex mixture into individual components. A mixture of gas components is injected into a chromatograph column, where the components travel down the column at different rates, reaching the end of the column at different times. A detector is positioned at the end of the column to quantify the concentrations of individual components of the mixture as they reach the end of the column.

The apparatus used in gas chromatography consists of four basic components: (1) a carrier-gas supply and flow controller, (2) a sample inlet system providing a means for introduction of the sample, (3) the chromatographic column and associated column oven, and (4) the detector system. The column is the heart of the gas chromatograph. Typically the column is a glass or metal tube of that is 6 to 13 mm in diameter and 1 to 2 meters in length. The chromatic column is filled with a carrier gas, most commonly nitrogen or helium, though other gases such as carbon dioxide, argon, xenon, and hydrogen are occasionally used.

The detector produces a response that is proportional to component that is separated by column and is located at the end of the column. Different detectors may be utilized dependent upon the analyte of interest. Any one of many different types of detectors could be used, such as an ion mobility spectrometer (IMS), mass spectrometer, photo ionization detector (PID), flame ionization detector (FID), thermal conductivity detector (TCD), electron capture detector (ECD), flame photometric detector (FPD) or far UV absorbance detector (FUV).

Chromatography is a well known and accurate technique for identifying constituents in a gas mixture. However, these units tend to be large and expensive, and specialized training is required to use them effectively.

Ion Mobility Spectrometry (IMS)

The gaseous sample to be analyzed enters a spectrometer, where it is ionized by a radioactive source. The resulting positive and negative charged species are then accelerated over a short distance and the time-of-flight is determined. The IMS differs from mass spectrometer in that it operates under atmospheric conditions and does not need large and expensive vacuum pumps. Because of this, IMSs can be miniaturized.

Like Chromatography, IMS is well know and accurate. However, IMS units are large and expensive, and require trained personnel to make a measurement.

Mass Spectrometry

The principle of the mass spectrometer is similar to the ion mobility spectrometer, except a vacuum is required. The sampled gas mixtures are ionized, and charged molecular fragments are produced. These fragments are sorted in a mass filter according to their mass to charge ratio. The ions are detected as electrical signals with an electron multiplier or a Faraday plate. Low mass ions are displayed as a vertical line at the left end of a scale while heavy ions are displayed towards the right. The length of a line represents the quantity of that ion in the gas mixture.

Mass Spectrometry is well know and accurate. However, IMS units are large and expensive, and require trained personnel to make a measurement.

Electrochemical Sensors

There are a wide variety of electrochemical sensors, which can be classified in two basic groups called potentiometric, in which a voltage measured and amperometric, in which a current is measured. These sensors consist of a casing that contains a collection of chemical reactants (electrolytes or gels) in contact with the surroundings through two terminals, an anode and a cathode. For gas sensors, the top of the casing has a membrane which can be permeated by the gas sample.

The presence of the gas to be detected causes oxidization to take place at the anode and reduction to take place at the cathode. A current is created as the positive ions flow to the cathode and the negative ions flow to the anode. Gases such as oxygen, nitrogen oxides, and chlorine, which are electrochemically reducible, are sensed at the cathode while electrochemically oxidizable gases such as carbon monoxide, nitrogen dioxide, and hydrogen sulfide are sensed at the anode. Potentiometric measurements are performed under conditions of near-zero current. Amperometric sensors are usually operated by imposing an external cell voltage sufficiently high to maintain a zero oxygen concentration at the cathodic surface. Sensitivity of amperometric sensors is generally better than potentiometric sensors.

Electrochemical sensors are wide-spread, but are typically too large and require too much power for portable applications. In addition, these sensors typically utilize toxic materials that are not suitable for portable applications.

Fiber Optic Sensors

Fiber optic sensors are a class of sensors that use optical fibers to detect chemical contaminants. Light is generated by a light source and is sent through an optical fiber. The light then returns through the optical fiber and is captured by a photo detector. Some optical fiber sensors use a single optical fiber while others use separate optical fibers for the light source and for the detector.

There are three general classes of fiber optic sensors The first type is completely passive. A spectroscopic method can be used to detect individual types of contaminants. This method involves sending a light source directly through the optical fiber and analyzing the light that is reflected or emitted by the contaminant. A second class of fiber optic sensors consist of a fiber optic sensor with a chemically interacting thin film attached to the tip. This film is formulated to bind with certain types of chemicals. Contaminant concentration can be found by measuring the color of the thin film, the change in refractive index, or by measuring the fluorescing of the film. The third type of fiber optic sensors involves injecting a reagent near the sensor. This reagent reacts either chemically or biologically with the contaminant. The reaction products are detected to give an estimate of the contaminant concentration.

These types of sensors have the advantage of power. Several types have no moving parts. They are also capable of detecting various chemicals at very low concentrations. However, they are limited by the ability to transmit light through the optical fiber over long distances. Some organic pollutants are not easily differentiated using UV-visible spectroscopy.

Colorimetry

Colorimetric devices work by analyzing the color of contaminated water that has been mixed with a particular chemical reagent. Pre-measured, unit-dose reagent that react with water samples are available for sale. To test water samples, the pocket colorimeter compares a reacted sample with a sample blank and yields results in concentration units.

Pocket colorimeter test kits are portable and are simple to use. They provide visual evidence of a gas detection event, and they are not prone to interferences. However, these devices have limited chemical sensitivity to individual VOCs. They also need actual water samples for testing, and cannot therefore be used in situ. Most kits do not meet U.S. EPA method requirements and may not be used for compliance monitoring.

Infrared Sensors

Infrared sensors can be used to detect gases, which, in general, have unique infrared absorption signatures in the 2-14 um range. The uniqueness of the gas absorption spectra enables identification and quantification of chemicals in liquid and gas mixtures with little interference from other gases. These devices are typically comprised of a source of infrared radiation, a detector capable of seeing the infrared radiation, and a path between the detector and source that is exposed to the gas being detected. When gas in the path absorbs energy from the source, the detector receives less radiation than without the gas present, and the detector can quantify the difference.

Mass Sensor-Surface Acoustic Wave Sensors/Portable Acoustic Wave Sensors

Surface Acoustic Wave Sensors (SAWS) are small miniature sensors used to detect VOCs. A SAW device consists of an input transducer, a chemical absorbent film, and an output transducer on a piezoelectric substrate. The piezoelectric substrate is typically quartz. The input transducer launches an acoustic wave which travels through the chemical film and is detected by the output transducer. The device runs at a very high frequency, generally about 100 MHz. The velocity and attenuation of the signal are sensitive to the viscoelasticity as well as the mass of the thin film which can allow for the identification of the contaminant. Heating elements under the chemical film can also be used to desorb chemicals from the device. A signal pattern recognition system that uses a clustering technique is needed to identify various chemicals.

SAWS have been able to distinguish organophosphates, chlorinated hydrocarbons, ketones, alcohols, aromatic hydrocarbons, saturated hydrocarbons, and water. They are small, low power, have no moving parts other than the high-frequency excitation, and are known to have good sensitivity to various chemicals, able to detect chemicals in very low concentrations. However, they are generally not able to discriminate among unknown mixtures of chemicals.

Metal-Oxide Semiconductor Sensors

Metal oxide sensors are the among the earliest and most popular sensor element in sensor arrays. For example, oxygen sensors used in every automobile are metal oxide sensors. A metal oxide sensor is an n-type inorganic semiconductor, such as tin oxide, doped tin oxide derivatives, zinc oxide, or iron oxide. These materials are heated to temperatures of 300 C. to 550 C. and used as a two-terminal resistive device. The response arises from the reduction of the gas species at the surface of the semiconductor which increases the electron carrier concentration, resulting in higher conductivity. The gas species is consumed as the sensor operates.

The sensor is traditionally constructed using a ceramic support tube containing a platinum heater coil and the metal oxide is coated onto the outside of the ceramic tube with the appropriate electrical leads connected to the film. In recent decades, newer implementations of the metal oxide sensor have been constructed with planar configurations using conventional micro-fabrication techniques. While using micro-fabrication methods is advantageous, there is a significant challenge with integration of multiple sensor elements into a single array. The procedure can be difficult and expensive due to extensive subtractive processes arising from materials compatibility across the different elements. In addition, there are complicating issues related to its high operating temperature.

Another disadvantage of the metal oxide is power consumption. Because the sensing response depends directly on the reduction reaction, which is very sensitive to the temperature, the sensor must be heated to at least 300 C. Generating such high temperatures is consumption, typically around 800 mW. Yet another disadvantage is a general lack of discrimination since the combustion mechanism limits the sensitivity of the device and is not reliant on the chemistry of the gas species itself.

Despite the these disadvantages of power consumption and integration, the metal oxide is by far the most commonly used gas sensor in commercially available electronic noses. The sensor is rugged and rather versatile and is already used in many other industrial settings. Of those that are often used for industrial applications, the tin oxide sensor doped with palladium or platinum is the most popular. However, the use of metal oxides continues to pose a fundamental problem of difficult integration.

Polymer-Absorption Chemiresistors

The concept of using polymeric absorption to detect the presence of chemicals in the vapor phase has existed for several decades. These polymer-absorption sensors, also called chemiresistors, consist of a chemically sensitive absorbent that is deposited onto a solid phase that acts as an electrode. When chemical vapors come into contact with the absorbent, the chemicals absorb into the polymers, causing them to swell. The swelling changes the resistance of the electrode, which can be measured and recorded. The amount of swelling corresponds to the concentration of the chemical vapor in contact with the absorbent. The process is reversible, but some hysteresis can occur when exposed to high concentrations. Several companies and organizations have developed chemiresistors, but the specific attributes and types of absorbents, which are generally proprietary, vary among the different applications.

Chemiresistors are attractive because they are small, low power devices that have no moving parts and have good sensitivity to various chemicals. However, these types of sensor generally react to a broad array of analytes, making it difficult to identify a specific gas. Some polymers react strongly to water vapor and moisture. Although the reaction with the analyte is designed to be reversible, the signal may experience hysteresis and a shift in the baseline over time when exposed to chemicals.

Conducting Polymer Sensors

A conducting polymer sensor is based on a polymer material possessing electrical properties that can selectively absorb specific odorants. Exposure to a gas analyte induces changes in the electrical behavior of the sensor. The sensor response arises from intermolecular interactions between the sensor and the analyte. These interactions are the result of hydrogen bonding, dipole-dipole or dipole-induced dipole dispersions, and hydrophobic forces. For this reason, conducting polymer sensor array are considered the most similar to the olfactory sensor of a biological nose.

The most popular materials is polypyrrole, a key feature of the polymer of which is the repeating and alternating arrangement of double bonds throughout the molecule. This feature, known as a conjugated pi electron system, gives rise to the electrical behavior. Reduction and oxidation of the polymer can subsequently modify its charge conducting behavior and it is surmised that the sensor response may result from reduction and oxidation processes or similar interactions involving partial charge transfer. Polypyrrole is most often deposited using electrochemical polymerization in order to avoid solvent compatibility issues. The properties of the film are strongly affected by the growth conditions but with careful control, purified and reproducible films can be achieved.

Conducting polymer sensors have several advantages. In general, they respond to a broad range of organic vapors and there is a large spectrum of materials that can be synthesized allowing for a wide range of selectivity. There are synthesized using relatively low cost materials and the sensor element can be fabricated with an attractive form factor. Unlike metal oxide sensor, conducting polymer sensors operate at room temperature, reducing power consumption and providing for longer lifetime.

A major disadvantage of a conducting polymer sensor is they tend to be sensitive to humidity and show a long-term drift in their performance. Further, they do not generally display a high specificity to individual gases. However, these polymers can be chemically tailored to enhance differences to response to classes of molecules.

ChemFET Sensors

A Chemically sensitive FET, also known as a ChemFET, is the structural analog of a MOSFET, with the polysilicon gate replaced with a chemically sensitive layer. The gate is chosen such it reacts with the gaseous species to cause a work function shift that can be detected through FET operation. Though ChemFETs are amenable to CMOS integration, in practice fabrication is greatly complicated since most polymers are electrochemically deposited.

Therefore, it would be desirable to provide a sensor that overcomes the drawbacks of the prior art to make it suitable for low-cost, low-power, wide-spread, and portable applications.

SUMMARY OF THE INVENTION

A key attribute to reducing the cost of sensor technology is integration into a standard silicon CMOS process. Traditional sensor technologies, however, are not conducive to direct implementation directly on silicon, due to material incompatibility, deposition incompatibility, or operating temperature.

As can be seen from the description of the sensor technologies described above, the technology that lends itself best to simple integration into a CMOS silicon fabrication process are the sensors based on polymers. For this reason, polymer-based sensors are among the most promising technologies for an entry into high-volume, low-cost sensor markets. However, as discussed above, these sensor technologies have limitations. The polymer technology as set forth in accordance with the present invention addresses these shortcomings.

One or more embodiments of the invention described herein may be implemented employing improvements to a sensor cell as described in U.S. Pat. No. 7,397,072 (and as is shown in FIG. 1), and a method of implementation of that improved cell. This improved cell structure allows measurement of two electrical signals, namely the current through the silicon transistor (a current reading between ss 208 and sd 206 in FIG. 2) and the polymer current (a current reading between os 204 and od 203 in FIG. 2). Of course, other sensor cells that may include similar electrode positioning may be employed in accordance with the invention as appropriate and desired. Each of these two currents represents a different analyte characteristics. These currents are preferably measured at the same instant of time, and therefore are different representations of same analyte concentration of the measured gas.

The silicon current is caused by minority carriers in the silicon 210 that are attracted to charge trapped in the polymer, thereby changing the threshold of the MOS device. This change of threshold gives rise to a change in current at any given source/drain voltage.

The change in current through the organic material is a measured by electrodes, which are in contact with the organic polymer. The resulting polymer current (Ios 204-Iod 203) is representative of a change in resistance of the polymer due to analyte interaction. As will be seen later, these two currents about the analyte will become part of the "vapor signature" of the vapor, including an analyte, being detected. The fact that this sensor cell offers two different currents to represent a given analyte enhances the uniqueness of the vapor signature for a given analyte, and will translate to simpler post-measurement analysis to identify the analyte.

The Sensor Cell Array:

The precise value of these currents will depend on how much analyte interacts with the polymer in the sensor cell. This interaction can be controlled for any given cell by adding certain receptor molecules, the interaction with a given analyte thereby being increased or otherwise modified. A given receptor molecules are preferably designed to attract a certain class of chemicals. The sensing materials are organic semiconductor polymers doped with a small molecule receptor, but can also be other types of polymers such as insulator polymers with carbon nanoparticles. All sensor materials used are solution-based, allowing low-cost deposition methodologies such as inkjet printing.

Therefore, in accordance with the present invention, a plurality of these receptor-doped sensor cells, each with a different receptor molecule, or different levels of a single molecule, may be placed into an array. Applied to such an array, each component of a vapor being measured will give rise to a different silicon and polymer current from each of the receptor-doped sensor cells of the array, the accumulation of which make up an "electronic signature" of the vapor. This electronic signature can then be compared to previous measurements to identify the same vapor or components of the same vapor.

Analyte Control in the Sensor Cell:

Heating of a receptor in, for example, a sensor cell of the present invention, will cause the analyte and the receptor to dissociate. For this reason, in many traditional sensor systems the sensor is placed on a heating pad. After a given measurement is complete, heat is applied to the sensor, releasing the analyte. Gas is also purged away from the sensor surface. The cell is then now ready for another measurement. Such mechanisms around the sensor significantly raise the cost of the sensor system, and also require time between measurements, thus reducing the number of tests that may be performed in a fixed period of time. The sensor cell incorporated into the present invention, on the other hand, offers several advantages in controlling the analyte introduction into the cell that come about due to the ability to control the electric field in the polymer.

Due to the structure of the inventive sensor cell, the vertical electric field through the polymer can be controlled. When the electric field induces a positive charge on the polymer, the analyte is absorbed into the polymer. When the electric field is reversed, the analyte is repelled from the polymer. Therefore, the control of the electric field in the sensing polymer of the cell reduces the need for valves and piping systems to bring the analyte to and from the sensing surface.

Since these cells are preferably built directly into the silicon substrate, it is possible to utilize an n+ diffusion runner in p-type substrate or a p+ diffusion running in n-type substrate to act as a localized heating source. Current running through the diffusion will generate sufficient heat to further dissociate the analyte and the receptor in the localized area while reducing overall hardware cost and time for heating.

Sensor Cell Array Architecture with Interchangeable Reference Cell:

The attributes of the inventive sensor cell described above lend itself to the inventive array architecture constructed in accordance with an alternative embodiment of the invention that results in substantial technical advantages over other cell systems. A diagram of this array architecture is shown in FIG. 4, and will be described in greater detail below.

In accordance with this embodiment of the invention, the sensor array preferably consists of two or more substantially identical columns of sensor cells, each column consisting of individual cells with a polymer sensor sensitive to different analytes. All or some of the sensor cells of one or more of the columns may be heated by the localized heating method described above. One or more columns of sensors are preferably not heated. The collection of all silicon and polymer cell currents in each column or array may generate a "vapor signature", but vapor signatures of each column may differ in response to differences in the sensor temperature. The comparison of the vapor signatures at the various heated and unheated columns and/or cells thereof may then be compared for the following purposes:

Continuously Updated Baseline:

At elevated temperatures, the analyte and the receptor are far less likely to bond. Therefore, the current generated in the heated sensors can act as a baseline in comparison to the sensor cells at room temperature. In traditional sensor arrays, the baseline is generated by a measurement made by the same sensor at a previous time. In this embodiment of the present invention, the baseline is continuously updated at the very same time as the analyte is measured with the unheated sensor, giving rise to several benefits:

(1) The measurement will be more accurate since the baseline is measured at the same time as the analyte measurement, eliminating errors created due to the time shift between the baseline measurement and the analyte measurement.

(2) Automated calibration to moisture.

(3) The analyte measurements can be taken at more frequent intervals, or even continuously, since there is no need to stop the sensor measurement to re-establish a baseline.

Activation Energy Information:

Activation energy is a measure of the temperature dependence of a chemical reaction. Specifically, when $\ln(x)$ vs $1/T$ is plotted, the slope of that equation is the activation energy $E_a$. This information can be obtained for both the silicon device and the organic device of the sensor cells. Since activation energy is specific to the type of analyte, this information helps significantly in identifying the analyte with reduced signal analysis.

Reduction of Signal Noise Due to Moisture:

Polymer materials are known to pick up moisture over time, changing the baseline signal. This change in baseline signal will add onto a previously measured vapor signature, giving rise to a different level. The moisture issue is traditionally resolved by periodically heating the sensor cells. During this heating time, the sensor array is traditionally unable to make any measurements. In the case of the inventive array architecture, however, moisture is removed by periodically changing the heated and unheated column.

Thus, in accordance with the invention, the proposed electronic nose consists of an array of sensors, each of which will yield a "signature" of the analyte being sensed at any given period of time by means of a current level. A series of such current level measurements may ultimately be used to identify a particular analyte. Current levels, however, are difficult to read with currently available digital circuitry, and are even harder to store. The present invention overcomes these drawbacks. Therefore, in accordance with the present invention, an improved method and apparatus for sensing gasses is provided employing an array structure of receptor cells to provide a vapor signature for one or more tested gasses.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 2:
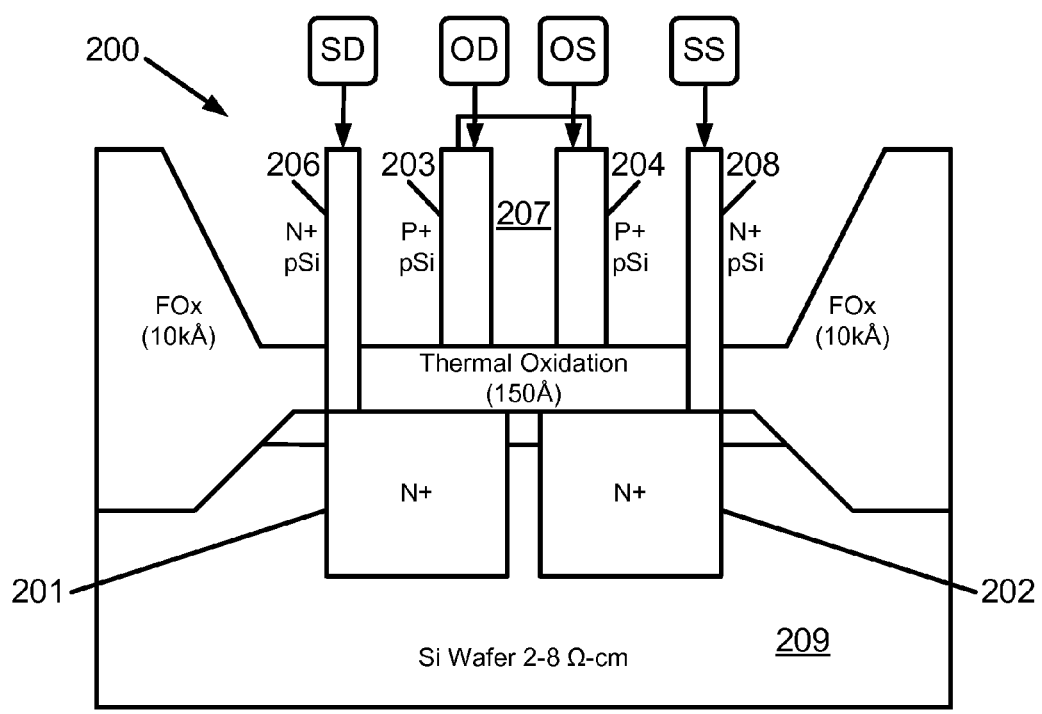
FIG. 2 is a cross section of an improved cell structure in accordance with an embodiment of the invention.

The invention will now be described making reference to the following drawings in which like reference numbers denote like structure. Referring to FIG. 2, an illustration of a cell structure that improves over prior art U.S. Pat. No. 7,397,072, and is constructed in accordance with an embodiment of the present invention, is shown. As is shown in FIG. 2, N+ regions 201 and 202 extend underneath the P+ Poly Si electrodes 203 and 204 and above silicon wafer 209. Such placement of the N+ regions provides an advantage of a channel underneath the P+ poly silicon electrodes 203 and 204 regardless of the potential of those electrodes. This inventive structure allows measurement of two electrical signals, namely the current through the silicon transistor (denoted "I(SS)–I(SD)", and comprising a measure of current flow between the SS electrode 208 and the SD electrode 206) and the current through the polymer (denoted "I(OS)–I(OD)", and comprising a measure of the current flow between the OS electrode 204 and the OD electrode 203.

Each of these two currents represents a different analyte characteristic. These currents are preferably measured at the same instant of time, and therefore comprise different representations of a same analyte concentration of a measured gas. The silicon current flow (the current measured between SS 208 and SD 206) is caused by minority carriers in the silicon that are attracted to charge trapped in the polymer, thereby changing the threshold of the MOS device. This change of threshold gives rise to a change in current at any given source/drain voltage. The change in current through the organic material is measured by electrodes 203 and 204, which are in contact with the organic polymer 207. The current through the polymer results from a change in resistance of the polymer due to analyte interaction. As will be described below, these two currents will become part of the "vapor signature" of the vapor being detected. Providing two different currents to represent a given analyte enhances the uniqueness of the vapor signature for a given analyte, and will translate to simpler post-measurement analysis to identify the analyte.

The precise value of these currents will depend on how much analyte interacts with the polymer 207. This interaction can be controlled for any given cell by adding certain receptor molecules, the interaction with a given analyte can be increased. A given receptor molecules are designed to attract a certain class of chemicals. The sensing materials are organic semiconductor polymers doped with a small molecule receptor, but can also be other types of polymers such as insulator polymers with carbon nanoparticles. All sensor materials used are solution-based, allowing low-cost deposition methodologies such as inkjet printing.

Figure 3:
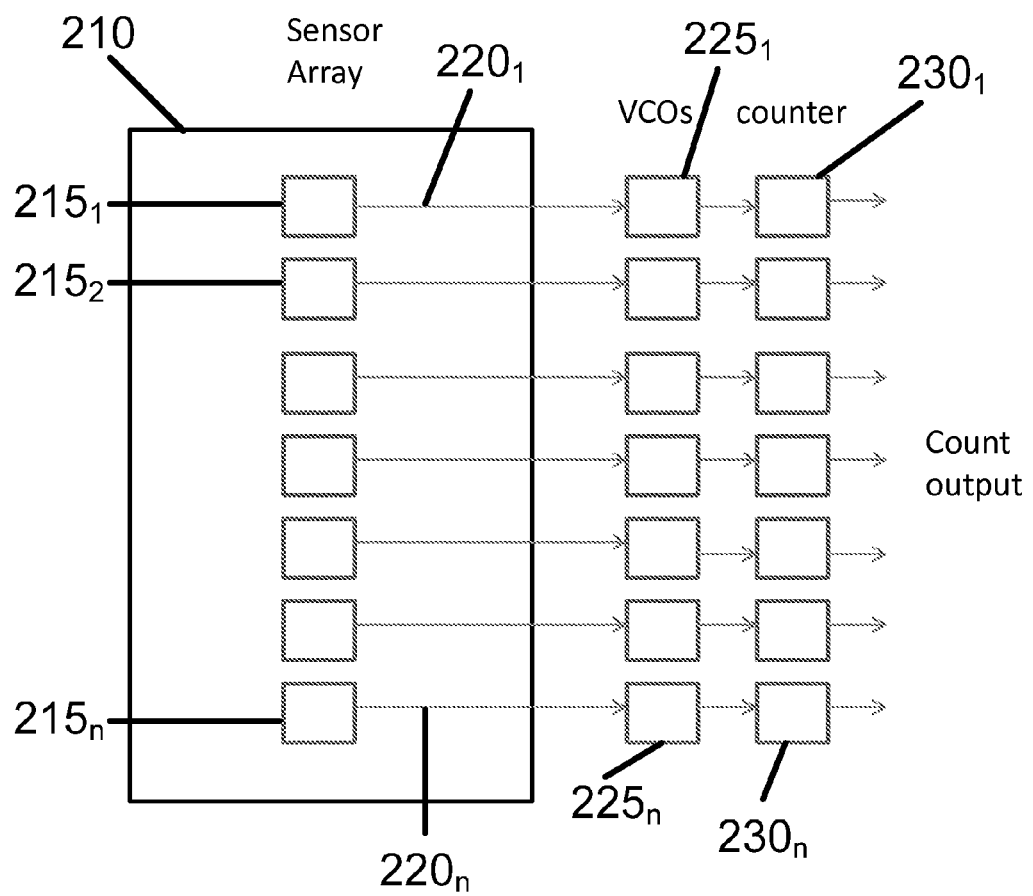
FIG. 3 is a sensor array constructed in accordance with an embodiment of the present invention.

Therefore, in accordance with the present invention, a plurality of these receptor-doped sensor cells, each with a different receptor molecule, or different levels of a single molecule, may be placed into an array, as is illustrated in FIG. 3. Applied to such an array, each component of a vapor being measured will give rise to a different silicon and polymer current from each of the receptor-doped sensor cells of the array, the accumulation of which make up an "electronic signature" of the vapor. This electronic signature can then be compared to previous measurements to identify the same vapor or components of the same vapor. As discussed above, this vapor signature consists of two currents from a series of sensor cells in an array. However, these currents are difficult to store and to compare to other vapor signatures. For this reason, these signals are converted to a digital format. One skilled in the art would employ Analog-to-Digital (A-to-D) converters for this purpose. However, it is desired to find circuitry that can fit on the pitch of the array so that the array itself will output the vapor signatures. Such a design would bring about design simplifications that will results in significant cost reductions of the final product.

Referring next to FIG. 3, a method and apparatus are disclosed in which a Voltage Controlled Oscillator (VCO) is used to convert a current level to a frequency. As the current level increases, so does the frequency, and vice versa. A counter is the used to count the number of oscillations per unit time. These values are then stored and used as a signature to determine a given analyte.

Figure 1:
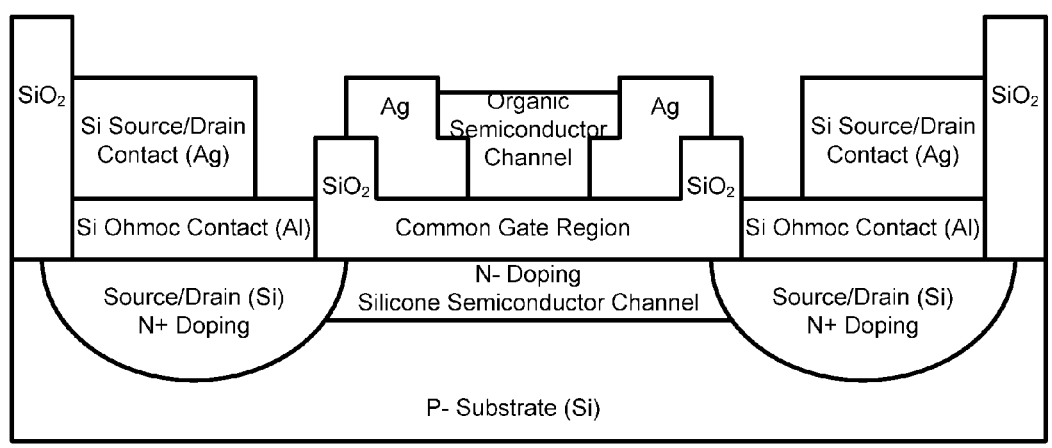
FIG. 1 is cross section of a prior art four-terminal FET chemical sensor device as described in U.S. Pat. No. 7,397,072.

In FIG. 3, a sensor array 210 is provided with one or more sensor elements $215_1 \ldots 215_n$. Each sensor element is preferably of the type depicted in FIG. 1, but may employ any type of desired sensor design. Each sensor from the sensor array preferably provides a corresponding current level output $220_1 \ldots 220_n$ related to the level of gas or other material sensed. This output relationship is preferably known for each sensor employed. It has been determined that such current output may also vary over time in accordance with various characteristics of the sensor, including but not limited to temperature, amount of time a gas has been in contact with the sensor, and the like.

Output current $220_1 \ldots 220_n$ from one or more of sensors $215_1 \ldots 215_n$ is then forwarded to corresponding Voltage Controlled Oscillators (VCOs) $225_1 \ldots 225_n$. Such voltage controlled oscillators provide an output oscillation, the frequency of which varies directly in accordance with an input current. Therefore, in accordance with the invention, as each sensor detects an amount of a gas to which it is sensitive, the sensor outputs a related current. This current is provided as an input to the corresponding VCO, which is then caused to generate an oscillating output related to the level of the current input. As is further shown in FIG. 3, this oscillating output is in turn provided to a corresponding counter $230_1 \ldots 230_n$. Each counter 230 thus counts a number of oscillations output from corresponding VCO 225 for a predetermined period of time. Such total counted number of oscillations per unit time is therefore indicative of the amount of gas sensed by corresponding sensor 215 over that period of time. These counts can then be stored in conventional memory 240 and preferably are stored associated with various identifying data, including counter identifier, time period identifier, time period duration, and any other desired information that would allow for the later processing of such stored count data to aid in analyzing detected gas concentration.

This method and apparatus allows the cells to be placed together in compact form, and permits signal control of the cells with row-oriented and column-oriented runners through the array that connect appropriately to the cell, much like a memory array. The VCO/counter circuitry sits on the periphery of the array, making the design efficient in terms of area utilized. This reduction in area may result in significant cost reduction.

Figure 4:
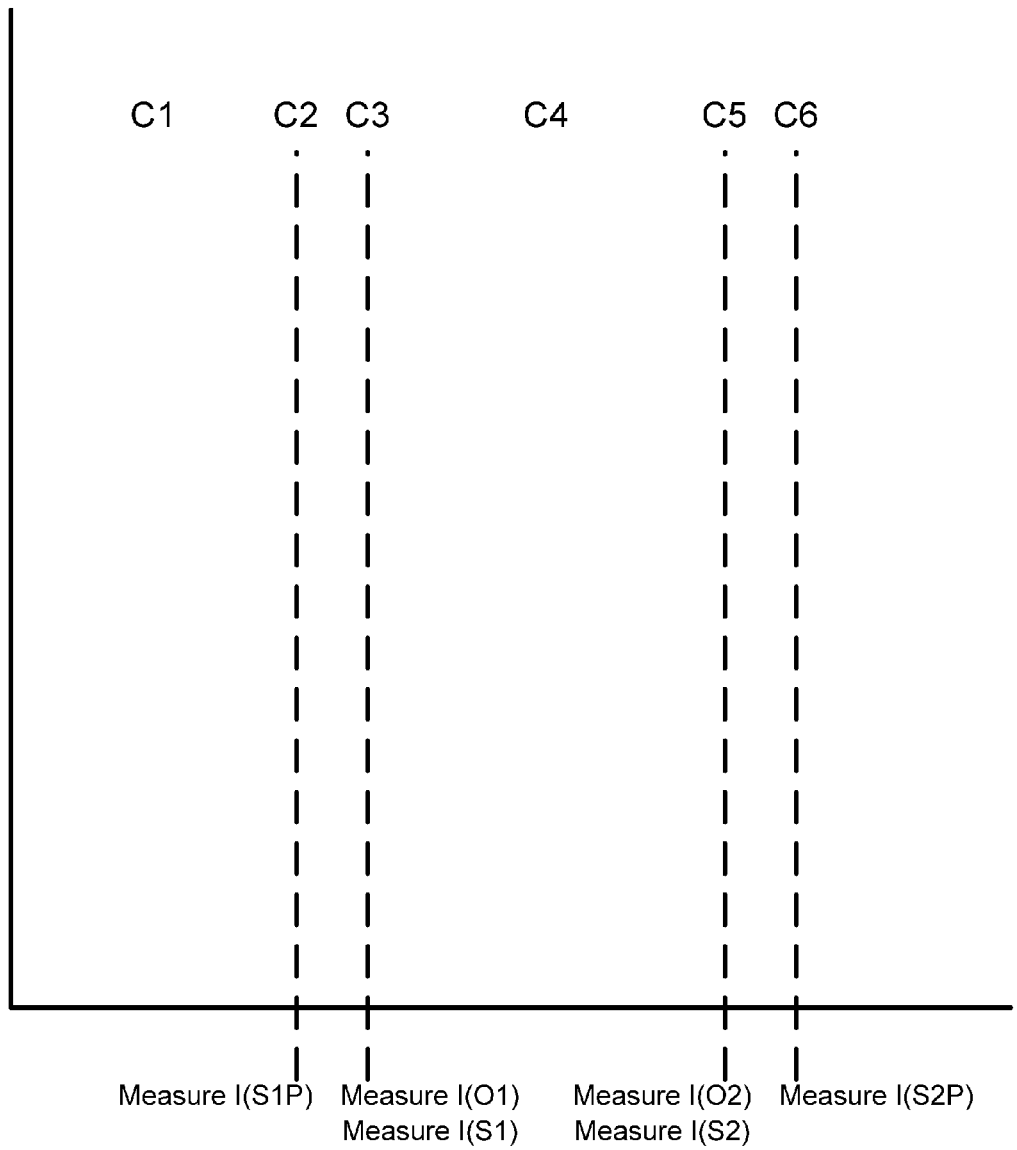
FIG. 4 is a timing diagram depicting an inventive sequence of measurements in accordance with an embodiment of the invention.

The cells in this array are biased in a particular manner to sense the analyte, to let the analyte accumulate, and to clear the analyte from the sensor cell, also referred to as "reset". These sensor cells are continuously cycled through these functions. FIG. 4 presents a timing diagram to provide a note of the order of operation, and a general concept of relative timing, although such relationships in FIG. 4 are approximate and should not be considered to be precisely accurate or even necessarily desirably consistent during operation.

A sensing cycle in accordance with the present invention preferably consists of 6 steps, which are then preferably repeated each time a reading from the sensor is to be taken. Performing these steps will result in a set of output signals for each sensor cell. The combination of these output signals can then be utilized to identify a given analyte in a particular cell, or can be combined with outputs from one or more additional sensor cells to provide a more extensive test result to more specifically identify one or more analytes. In each step, the bias noted describes the voltage level at the particular noted physical location on the sensor cell In order to perform such an action, a bias is applied across the electrodes, and thus across the receptor of the sensor cell to aid in different desired movement of analyte material.

The first step, noted at timing C1 in FIG. 4, comprises a Reset Cycle. During this time period, the objective is to remove analyte from the receptor in the sensor cell. The Bias: SS=5 SD=5 OS=0 OD=0 insures that there is no current movement between SS and SD (as they are both maintained at approximately 5V), and there is also no current movement between OS and OD in that they are both maintained at ground. These values, however, do generate an electric field. As analyte is generally a negatively charged particle, the analyte is driven from the higher voltage of the SS and SD layer out past the OS and OD layer and out of the receptor in the sensor cell. No measurements are made from the sensor cell in this step.

The second step takes place at timing C2, with an objective to obtain the silicon current (SS-SD) at the start of analyte accumulation in a sensitive part of transistor regime and to quantify any drift due to changes in the materials used in the gas sensor cell. In particular the current of S1P, (I(S1P)) is determined by measuring the current between the SS and SD electrodes, so I(S1P)=I(SS-SD), to measure a silicon current signature before analyte accumulation in a most sensitive region. The notation of "P" here is intended to indicate that this measurement detects the change in Vt of the silicon transistor as a result of increased charge from the analyte, performed in a most sensitive regime of the transistor characteristics. The electrodes are charged so that SS=0 SD=1 OS=0 OD=0, and therefore there is a slight current flow from SS to SD, and no current flow from OS to OD. There is also no voltage gradient in the receptor of the sensor, and therefore analyte is neither drawn into nor expelled from the receptor. The measurement in this second step detects the change in Vt of the silicon transistor as a result of increased charge from the analyte, and indicator of analyte charge starting at a time when analyte movement into the receptor of the sensor cell, just at the threshold of detection thereof.

The third step takes place at timing C3 in FIG. 4, and in particular the objective is to obtain a measure of organic and silicon current signature immediately after analyte introduction, and therefore perform measurements of I(O1) and I(S1). In this step, the electrodes are biased so that SS=0 SD=1 OS=5 OD=3 so that there is current flow from SD to SS and from OS to OD. Furthermore, the voltage gradient set up between the organic electrodes (OS, OD) and the silicon electrodes (SS, SD) aids to draw analyte into the receptor. I(S1)=I(SS-SD) is measured to determine the silicon current signature immediately after analyte introduction, and I(O1)=I(OS-OD) is measured to determine the organic current signature immediately after analyte introduction.

The fourth step takes place on the timing diagram at step C4, allowing for analyte accumulation. Analyte is attracted to the organic material due to a positive charge on sensor material, generated in accordance with the electrode bias that is unchanged from step C3 (SS=0 SD=1 OS=5 OD=3). Thus, analyte accumulation is encouraged during this time period, and while no measurements are necessarily planned, additional I(OX) and I(SX) currents may be measured during accumulation to aid in determining characteristics thereof.

After sufficient analyte accumulation, measurements of I(O2) and I(S2) are performed at a time C5 in FIG. 4 to obtain organic and silicon current signature after analyte accumulation. The silicon current measurement may be made simultaneously, or sequentially to the organic current to prevent cross-talk of the two measurements, as desired. Once again, the biasing currents are unchanged from the above steps, so that SS=0 SD=1 OS=5 OD=3. Measurement I(S1)=I(SS-SD) is made to determine the silicon current signature after analyte accumulation, and measurement I(O1)=I(OS-OD) to determine the organic current signature after analyte accumulation.

Finally, at step C6: a measurement of I(S2P) is made to obtain the silicon current after analyte accumulation in most sensitive part of transistor regime. Bias on the electrodes is changed so that SS=0 SD=1 OS=0 OD=0 so that while there is a small current flow from SS to SD, ther is no current flow from OS to OD, and there is no voltage gradient across the receptor of the sensor cell. I(S2P)=I(SS-SD) is then measured to determine the silicon current signature after analyte accumulation in sensitive regime Then, processing returns to step C1 for a next cycle of reading. Further, while this cycle is described with six steps in order, less steps may be employed, with a reduction in the number of measured values. Further, the order of the steps may be changed, as long as sufficient time is allowed between steps to allow for a steady state of analyte to be reached. Additionally, a reset step need not be performed each cycle, and may be performed less than every cycle, when necessary to clear the analyte from the sensor cell.

In a preferred embodiment, a plurality of sensor cells are provided in an array format, each preferably having different receptor portions. Thus, through the use of the above steps for multiple sensor cells, an analyte signature can be generated to aid in determining various characteristics thereof.

Figure 5:
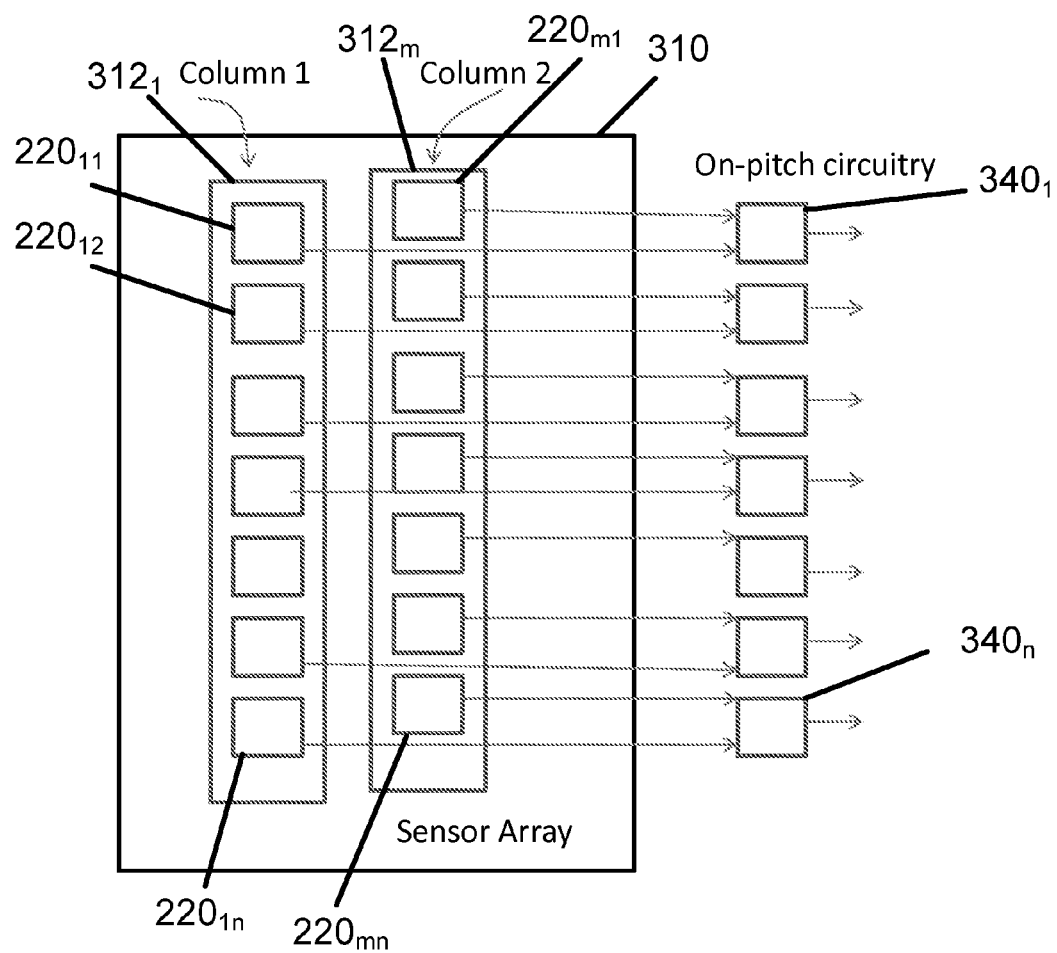
FIG. 5 is a sensor array constructed in accordance with an alternative embodiment of the invention.

Therefore, in accordance with the invention, a method for performing one or more measurements of the disclosed sensor cell, or variants thereof including similar electrode structure, is described. It is contemplated that a processor or other computing and calculation processor function to control this process, changing the electrode currents, storing and implementing the processing program algorithm, storing reading results and the like Referring next to FIG. 5, an alternative embodiment of the invention is shown. In FIG. 5, a sensor array 310, comprises two or more sensor columns $312_1 \ldots 312_m$, each sensor column 312 comprising one or more sensor elements $220_1 \ldots 220_n$, similar sensor elements to those described in accordance with FIG. 3. Thus, an m column, n sensor array is disclosed. Of course, the sensor elements need not be distributed in such a regular array, and indeed may be positioned in any desirable configuration. Each sensor 220 is then preferably connected to one or more on chip circuitry elements $340_1 \ldots 340_n$. It is contemplated that each of these on chip circuitry elements contains a input to receive a current output from one or more sensor cells 220, and further comprises a VCO 225 and corresponding counter 230 as described in relation to FIG. 3.

Each chip circuitry element may also include a switching element to switch input paths to be processed be the circuitry, thus effectively selecting from which sensor element 220 the circuitry is to receive a signal at a particular time. A more passive switching element may be available if the various output signal from the sensor elements 220 are themselves controlled so that only one sensor element is outputting a signal to a particular circuit element 340 at a time. Furthermore, while on chip circuitry elements are described, it is contemplated that the use of such sensor array columns need not be so limited, and in fact the outputs from these sensor arrays may be provided to any type of counting or analysis mechanisms.

During use, one column of the array is preferably activated at a time to allow for sensor information to be provided to on chip circuitry elements 340, much in the manner as described in accordance with FIG. 3. After reading information for a predetermined time from a particular array column, it is then possible to switch and read further information from a second of the array columns, thus increasing the speed of the device. Thus, while one column of the device is reading information, the others may be resetting or be otherwise processed. For a situation where a large number of consecutive readings must be taken, a large number of array columns may be provided and used sequentially. While it is contemplated that each array column include a similar set of sensor elements, different sensitivity sensor elements may be provided to allow for more flexibility in testing.

Figure 6:
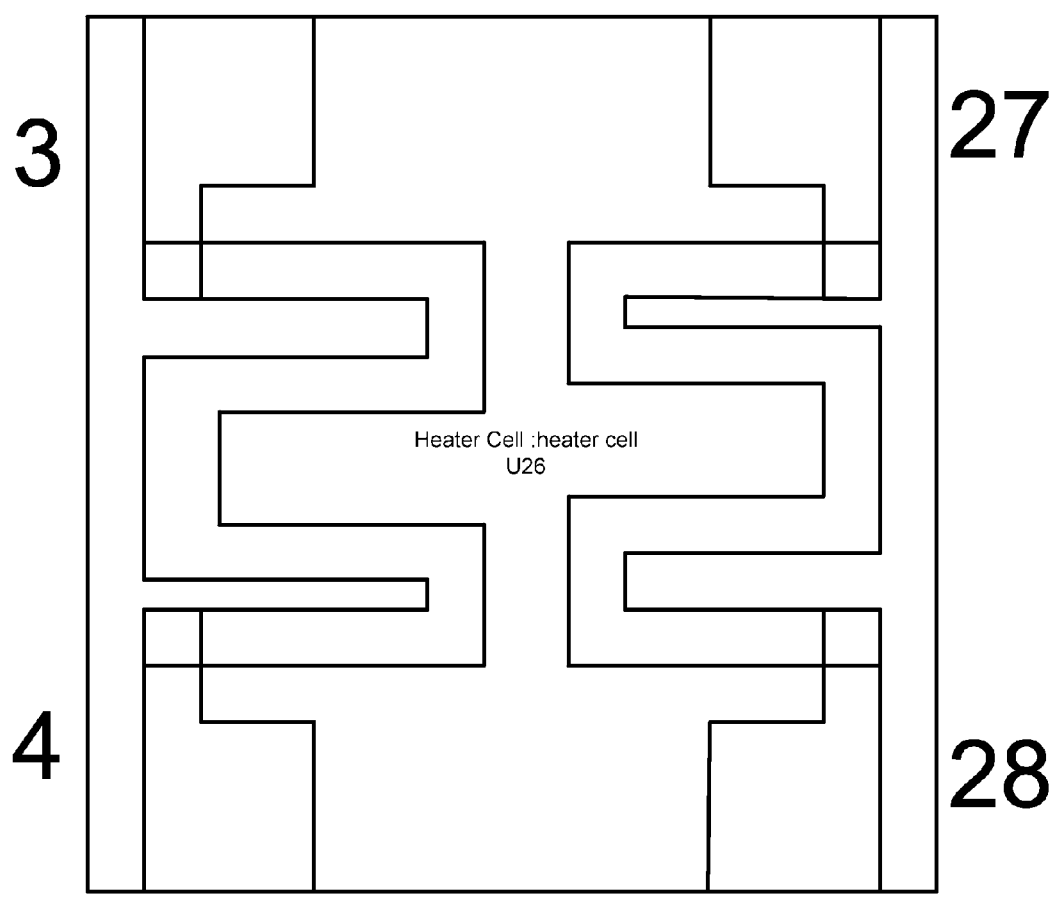
FIG. 6 is a layout of a cell heater in accordance with the invention.
Figure 7:
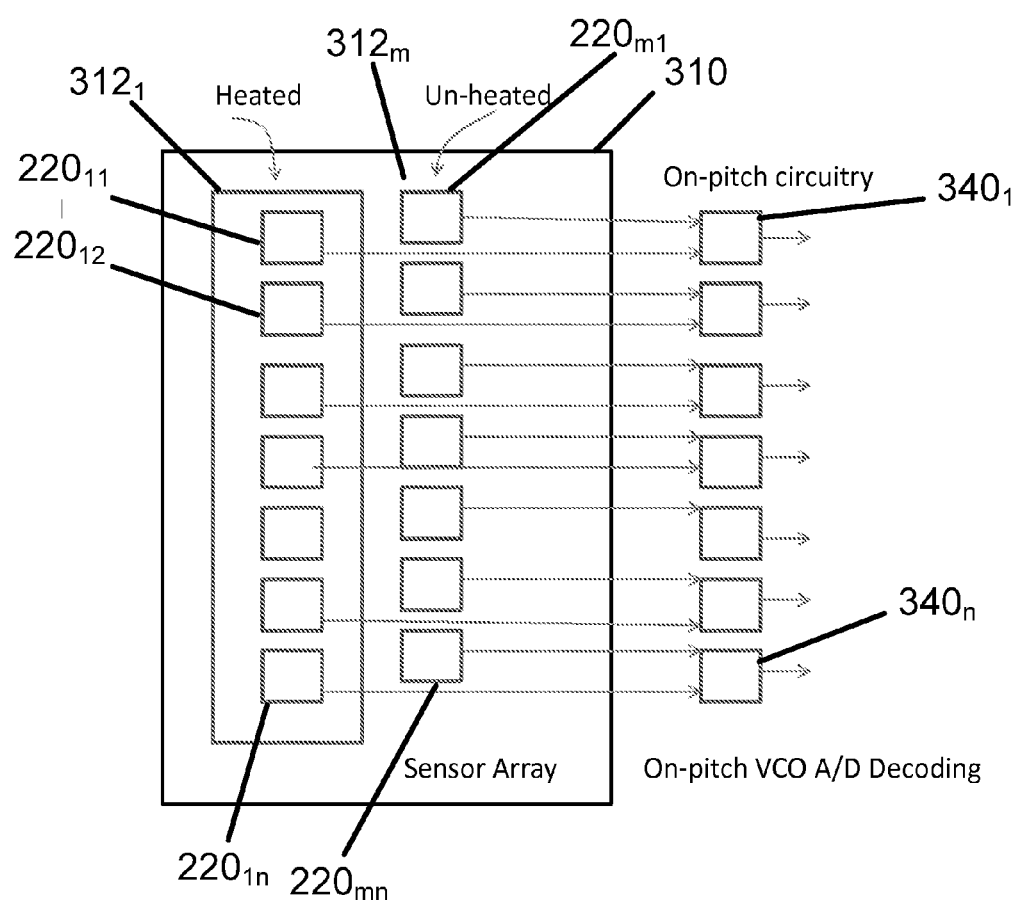
FIG. 7 is a sensor array constructed in accordance with an additional alternative embodiment of the invention.

Possible processing that may be applied to an array column may comprise application of an electrical field to the sensors, or heating the elements of a particular sensor or sensor array column, for the reasons noted above with respect to disassociation of the analyte and the receptor of the sensor cell. Referring next to FIGS. 6 and 7, such application of an electric current and heating of individual sensor cells or columns will be described.

Dissociation of the analyte from the receptor after a given measurement is completed can be achieved with an electric field perpendicular to the film surface to drive the analyte out. Due to the structure of the preferably employed inventive sensor cell, a vertical electric field through the polymer of each sensor element can be controlled. When the electric field induces a positive charge on the polymer, the analyte is absorbed into the polymer. When the electric field is reversed, the analyte is repelled from the polymer. Therefore, the control of the electric field in the sensing polymer of the cell reduces the need for valves and piping systems to bring the analyte to and from the sensing surface. Therefore, in accordance with the invention as set forth in FIG. 7, application of such an electric field can be applied to one or more of the individual sensors 220, or preferably to one or more of the sensor array columns 312 to attract the analyte thereto prior to sensor readings being made. However, in some cases the receptor binds to the analyte with sufficient strength that the electric field does not achieve complete dissociation. In these cases, it becomes necessary to heat the cell.

Traditionally, a separate heating pad is placed underneath the sensors. However, this method is bulky, expensive, and power-consuming. Therefore, as is shown in FIG. 6, a heating mechanism provided by placing an n+ in the vicinity each cell. When current is passed through this n+, resistive heating will raise the temperature of the area around it, thereby heating the sensor cells that are in the vicinity. In accordance with the invention, each of these n+ elements may be controlled individually, or may be alternatively controlled to act in concert for a particular array column, thus allowing the placement of sensor elements in an array column in close proximity to each other as they will be heated simultaneously, while allowing for the placement of the array columns to avoid heating of one column through the activation of the n+ heating elements associated with an adjacent sensor array column.

The benefits with this method of heating are two-fold: (1) this heat mechanism can be incorporated directly into the silicon chip, and (2) this method provides a local heat mechanism, permitting only the cells that require heating at any specific time to be heated.

Therefore, as is further shown in FIG. 7, one or more of the sensor array columns may be unheated (and also un electrified as noted above to remove analyte from the receptor. It is preferred that these sensor array columns be providing sensing information to the corresponding circuit elements 340, or other elements for accumulating information from the sensor arrays, as noted above. Other of the array columns may be heated, and/or electrified to drive the analyte form the receptors of the sensor cells in these sensor array columns, thus preparing these sensors or future sensing operations. As multiple array columns may be provided, various of these columns will be in different states, having been subject to electrical current and/or heating for different periods of time in accordance when they were last used for a sensing operation. Therefore in accordance with the invention, sensor array columns may be electrified and/or heated in sequence, or at a timing as desired to allow for the most efficient sensing operations to be undertaken.

In addition to preparing the sensors for future sensing operations, performing a sensing operation while a sensor element or sensor array column is being electrified and/or heated may be desirable. The use of such localized heating in a reference sensor cell may allow for a baseline reading to be taken at any time, thus improving the accuracy of the sensing apparatus. Such use of localized heating in a reference cell or reference sensor array column may bring about several key advantages, including but not limited to (1) a continuously-updated baseline; (2) a measure of the activation energy of the analyte to the receptor; and (3) an increase in the number of measurements per unit time.

The following process may allow for the use of one or more of the sensor array columns to be employed as a reference sensor array column. One or more columns of sensors is subjected to localized heat (and/or electrification) that is generated by passing current through n+ diffusion in a p-type silicon substrate (or a p+ diffusion in n-type silicon) that is routed in the vicinity of those sensors, as described in accordance with FIG. 6. One or more additional columns of substantially identical sensors may preferably not be subjected to this heat. A measure of the current between the source and drain off the silicon device and the source and drain on the organic device of each sensor is run to the periphery of the array, along the chip, and captured by circuitry 340. The silicon device currents of the heated and unheated devices and the organic device currents of the heated and unheated devices may then be compared to provide the above benefits, which will now be described in more depth.

At elevated temperatures, the analyte and the receptor are far less likely to bond. Therefore, the current generated in the heated sensors can act as a baseline in comparison to the sensor cells at room temperature. In traditional sensor arrays, the baseline is generated by a measurement made by the same sensor at a previous time. In accordance with the invention as set forth in FIG. 7, the baseline may be continuously updated at nearly the very same time as the analyte is measured with the unheated sensor, giving rise to several benefits:

(1) The measurement will be more accurate since the baseline is measured at the same time as the analyte measurement, eliminating errors created due to the time shift between the baseline measurement and the analyte measurement.

(2) automated calibration to moisture (3) The analyte measurements can be taken at more frequent intervals, or even continuously, since there is no need to stop the sensor measurement to re-establish a baseline.

Activation energy is a measure of the temperature dependence of a chemical reaction. Specifically, when ln(x) vs 1/T is plotted, the slope of that equation is the activation energy Ea. This information can be obtained for both the silicon device and the organic device of the sensor cells. Since activation energy is specific to the type of analyte, this information helps significantly in identifying the analyte with reduced signal analysis.

Furthermore, additional benefits of selectively heating one or more of the sensor cells is that the Polymer sensors preferably employed in accordance with the present invention are known to pick up moisture over time, causing the base signal for any given analyte to drift. This problem is generally resolved by heating the cell, thereby driving away moisture. Thus, each heated column is not susceptible to being affected by any such moisture accumulation since it is being heated. However, as moisture accumulates in the polymer the baseline signal of the unheated cell could drift. Thus, as described above, through the selective heating of individual sensor cells or sensor array columns, and in particular through the interchanging of heated and unheated sensor array columns, such drift issues may be eliminated.

In particular, in order to avoid such baseline drift, two or more substantially identical columns of sensor arrays are placed in an array, each with a capability of heating. In a first cycle, one or more of the columns are heated and others of the one or more columns are unheated. In a subsequent cycle, one or more of the previously unheated columns are heated, and one or more of the previously heated columns are unheated. Operation is altered between two or more such cycles at a frequency necessary to keep moisture levels in the cell sufficiently low to avoid baseline drift.

Therefore, in accordance with the invention, a sensor array constructed in accordance with one or more of the embodiments of the invention may be integrated into a standard CMOS silicon process, thus providing one or more of the following benefits over prior art sensor products.

Manufacturability:

The sensor cell can be integrated directly into CMOS silicon, and the sensing polymers are solution based allowing low cost high volume deposition methods.

Increased Signal Information from Each Sensor Cell:

Signals convey information about the analyte's charge (silicon current), size (polymer current), and activation energy (comparison between signals at two different temperatures). This increased information may result in better analyte selectivity and reduced need for signal analysis.

Control Over Analyte/Receptor Interaction:

The cell structure allows the charge of the polymer to be controlled by an electric field, attracting or repelling the analyte from the sensor measurement surface.

Increased Immunity from Sensor Drift:

The measured sensor cell is compared to the same cell at a high temperature, giving rise to a continuously updated baseline signal, increasing immunity to sensor drift.

Moisture Resistance:

One of two identical columns of sensor cells are heated while the other column is being measured, and are swapped with sufficient frequency so that moisture build-up in either column of cells becomes a problem.

Receptor Diversity:

In addition to organic semiconductor polymers doped with a receptor, the cell structure can accommodate a wide variety of different polymer-based sensing materials.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. An apparatus for sensing analyte, comprising:
   a plurality of sensor array columns, each sensor array column comprising a plurality of sensors, each sensor being adapted for sensing one or more parameters in reaction to the presence of one or more analytes and output a current therefrom in accordance with level of the sensed parameter;
   a heating element for selectively heating one or more of the sensor array columns;
   a Voltage Controlled Oscillator (VCO) array comprising a plurality of VCOs, each VCO adapted to receive an output current from one of the plurality of sensors from each of the plurality of sensor arrays and for and generating an output oscillation frequency in accordance with the level of the received output current; and
   a counter array comprising a plurality of counters, each counter adapted to receive an output from a corresponding VCO and count a number of oscillations over a predetermined time;
   wherein the heating element comprises an n+ resistive heating element;
   wherein one or more heating elements are provided to selectively heat one or more of the sensor array columns;
   wherein during operation, one or more of the sensor array columns are heated, and one or more of the sensor array columns are not heated; and
   wherein each counter of the counter array selectively determines a number of oscillations from each of a corresponding sensor element from one of the non-heated sensor array columns over a first predetermined time, and determines a number of oscillations from each of a corresponding sensor element from one of the heated sensor array columns over a second predetermined time.

2. The apparatus of claim 1, wherein the determined number of oscillations from each of the corresponding sensor element from the one of the heated sensor array columns over the second predetermined time comprises a baseline sensor array reading.

3. The apparatus of claim 1, wherein, after a predetermined period of time, at least one of the sensor array columns that was heated is not heated.

4. The apparatus of claim 1, wherein, after a predetermined period of time, at least one of the sensor array columns that was not heated is heated.

5. The apparatus of claim 1, wherein, after a predetermined period of time, the sensor array columns that were not heated are heated, and the sensor array columns that were heated are not heated.

* * * * *